United States Patent
Buchholz et al.

(10) Patent No.: US 6,514,527 B1
(45) Date of Patent: Feb. 4, 2003

(54) COMPOSITIONS COMPRISING A MIXTURE OF BIOFLAVONOLS

(75) Inventors: Herwig Buchholz, Frankfurt (DE); Jerzy Meduski, Playa del Rey, CA (US)

(73) Assignee: Merck Patentgesellschaft, Darmstadt (DE)

(*) Notice: Subject to any disclaimer, the term of this patent is extended or adjusted under 35 U.S.C. 154(b) by 0 days.

(21) Appl. No.: 09/830,118
(22) PCT Filed: Oct. 16, 1999
(86) PCT No.: PCT/EP99/07865
§ 371 (c)(1), (2), (4) Date: Apr. 24, 2001
(87) PCT Pub. No.: WO22/25795
PCT Pub. Date: May 11, 2000

Related U.S. Application Data
(60) Provisional application No. 60/106,080, filed on Oct. 29, 1998.

(30) Foreign Application Priority Data
Mar. 22, 1999 (EP) ............................................. 99105035

(51) Int. Cl.⁷ .................................................. A61K 9/00
(52) U.S. Cl. ........................ 424/464; 424/725; 424/464
(58) Field of Search ................................. 424/724, 464, 424/400, 439, 457, 725

(56) References Cited

U.S. PATENT DOCUMENTS
5,240,732 A * 8/1993 Ueda ........................... 426/597

FOREIGN PATENT DOCUMENTS
| JP | 4099771 | 3/1992 |
| JP | 6199693 | 7/1994 |
| JP | 6199697 | 7/1994 |

OTHER PUBLICATIONS
Database WPI Section Ch, Week 199433 Derwent Publications Ltd., London, GB; AN 1994–269373 XP002129883 & JP 06 199697 A (Kato K), Jul. 19, 1994.

Hollmann P.C.H. et al: "Bioavailability of the dietary antioxidant flavonol quercetin in man" Cancer Letters, vol. 114, 1997, pp. 139–140, XP002129881 cited in the application.

Hollmann P.C.H. et al: "Relative bioavailability of the antioxidant flavonoid quercetin from various foods in man" Febs Letters, vol. 418, 1997, pp. 152–156, XP000872805 cited in the application.

Database WPI Section Ch, Week 199219 Derwent Publications Ltd., London, GB; AN 1992–157345 XP002129885 & JP 04 099771 A (San–Ei Chem Ind Ltd), Mar. 31, 1992.

Database WPI Section Ch, Week 199433 Derwent Publications Ltd., London, GB; AN 1994–26939 XP002129884 & JP 06 199693 A (Kato K), Jul. 19, 1994.

* cited by examiner

*Primary Examiner*—Jose' G. Dees
*Assistant Examiner*—Sharmila S. Gollamudi
(74) *Attorney, Agent, or Firm*—Millen, White, Zelano & Branigan, P.C.

(57) ABSTRACT

The present invention relates to novel compositions containing a mixture of two or three bioflavonols like isoquercetin, quercetin-4'-glycoside, rutin and quercetin, which show differences in their pharmacokinetics. These compositions are useful as food supplements possessing preventive properties against damage to human tissues due to their antioxidant properties. Furthermore, these compositions secure a continuum of the presence of bioflavonols having the same aglycone in human plasma over an extended period of time.

22 Claims, 1 Drawing Sheet

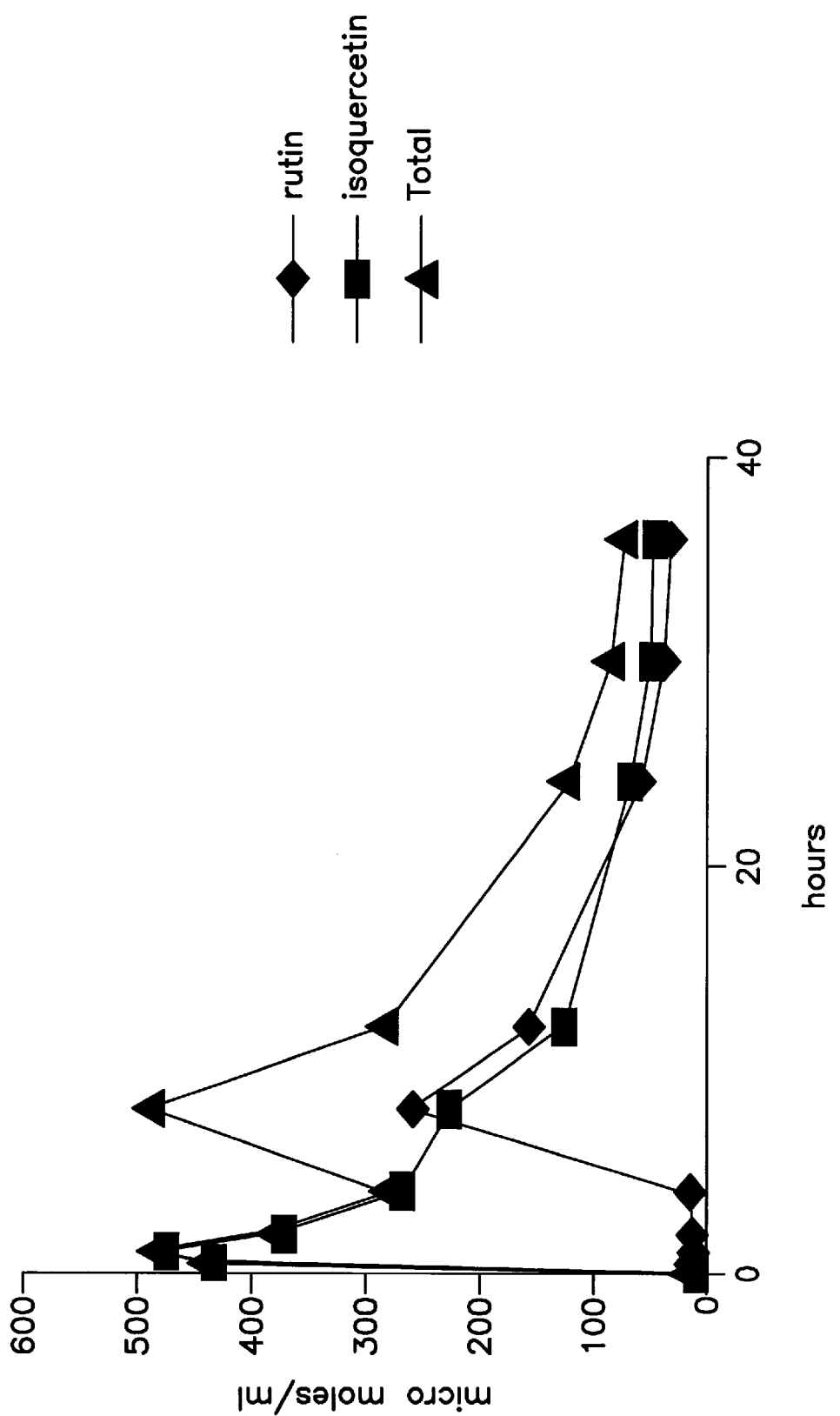

COMPOSITIONS COMPRISING A MIXTURE OF BIOFLAVONOLS

This application claims the benefit of priority of U.S. Ser. No. 60/106,080, filed Oct. 29, 1998.

The present invention relates to novel compositions containing a mixture of two or three bioflavonols like isoquercetin, quercetin-4'-glycoside, rutin and quercetin, which show differences in their pharmacokinetics. These compositions are useful as food supplements possessing preventive properties against damage to human tissues due to their antioxidant properties. Furthermore, these compositions secure a continuum of the presence of bioflavonols in human plasma.

Structures of body tissues are susceptible to damage caused by the oxidative stress, e.g., by the accumulation of reactive oxygen species during ageing, chronic environmental stress, inflammations or general metabolic dysfunctions. The role of reactive oxygen species in aetiology of human diseases (e.g. cancer, atherosclerosis, rheumatoid arthritis, inflammatory bowel diseases, immune system dysfunctions, brain function decline, connective tissue dysfunctions) is well established. Chronic exposure to reactive oxygen species leads to chronic intracellular damage, to oxidative stress and premature ageing. Cells of the human body possess metabolic antioxidant defences which are supported by dietary antioxidants. The early observations of the antioxidant defence metabolic processes involved flavonoids.

Quercetin, an aglycone, isoquercetin, a quercetin glycoside, and rutin, a quercetin rutinoside, are flavonols that are being recently extensively studied due to their antioxidant properties. Gycosylation of an aglycone makes the molecule less reactive towards free radicals and more water-soluble. Kind and the position of the glycosylation are the sources of the pharmacokinetic differences among flavonols that have the same aglycone.

Common glycosylation positions are: the 7-hydroxyl in flavones, isoflavones and dihydroflavones; the 3- and 7-hydroxyl in flavonols and dihydroflavonols; and the 3- and 5-hydroxyl in anthocyanidins. The sugar most usually involved in the glycoside formation is glucose, although galactose, rhamnose, xylose and arabinose also occur, as well as several disaccharides. For example, onions contain mostly isoquercetin, apples contain various quercetin glycosides, galactosides, arabinosides, rhamnosides, xylosides and glucosides. Many plants contain the quercetin disaccharide, rutin.

Flavonols are metabolized by animal cells, especially those of the liver. No residuals of flavonols are accumulated in the body (see Havsteen B. (1983), Flavonoids, a class of natural products of high pharmacological potency, Biochemical Pharmacology 32(7), 1141–1148).

Also absorption kinetics of flavonols is highly dependent on their chemical structure. The bioavailabilities of isoquercetin, rutin and quercetin differ. The bioavailability of rutin is only 30% of the bioavailability of isoquercetin. Hollman (see Hollman, P. C. H., et al. (1997) Bioavailability of the dietary antioxidant flavonol quercetin in man, Cancer Lett. 114: 139–140) explains the superior absorption of isoquercetin by the fact that isoquercetin is actively absorbed using sodium-glucose absorption mechanism. Quercetin is absorbed as an aglycone and is present in the human plasma in its free form (see Noteborn, H. P. J. M. et al. (1997) Oral absorption and metabolism of quercetin and sugar-conjugated derivatives in specific transport systems, Cancer Lett. 114:175–177; Conquer, J. A., et al. (1998) Supplementation with Quercetin Markedly Increases Plasma Quercetin Concentration without Effect on Selected Risk Factors for Heart Disease in Healthy Subjects, J. Nutr. March 1; 128(3): 593–597) and in the glycosylated forms when absorbed as a glycoside. It has been shown that quercetin is preferentially absorbed as its monoglucosides (see Papanga, G. Rice-Evans, C. A. (1997) The identification of flavonoids as glycosides in human plasma, FEBS Lett. 401(1): 78–82; and Hollman, P. C. H. et al. (1997) Relative bioavailability of the antioxidant flavonoid quercetin from various foods in man, FEBS Lett., November 24; 418(1–2): 152–156).

As expected all of these compounds, quercetin, isoquercetin, quercetin-4'-glycoside and rutin differ in their pharmacokinetics.

For orally administered isoquercetin the time to reach peak is about 0.70 h (see Hollman, P. C. H., (1997) Determinants of the absorption of the dietary flavonoid quercetin in man; Proefschrift). For the free quercetin the time to peak could be evaluated at about 3 h (see Da Silva, E. L., et al. (1998) Inhibition of mammalian 15-lipoxygenase-dependent lipid peroxidation in low-density lipoprotein by quercetin and quercetin monoglucosides, Archives of Biochemistry and Biophysics 349, (2) January 15, 313–320). For rutin the time was about 7 to 9 h (see Hollman).

After having reached the peak (after different periods of time), the concentration of the flavonols quickly decreases by metabolization.

Therefore, it is not possible so far to obtain a continuum presence of bioflavonols in the human plasma for an extended time span.

However, it would be desirable to have orally applicable formulation of these specific antioxidants leading to an increased and continued present concentration of bioflavonols having the same aglycone in the human plasma over a prolonged period of time.

Accordingly, there was a need for a composition useful for the enhancement of antioxidant activity in human plasma during an extended time span in order to prevent damage to human tissues.

Now it has been found that the mixture of two or three flavonols, when administered jointly to humans, will secure the very similar concentrations of flavonols in plasma assuring similar pharmacological and nutraceutical activity for an extended time period.

Object of the present invention is therefore an orally applicable composition comprising a mixture of the bioflavonols isoquercetin (quercetin-3-glucoside) or quercetin-4'-glucoside and rutin, optionally together with quercetin.

It has been found that a mixture of isoquercetin or quercetin-4'-glucoside, quercetin and rutin in the molar ratio of 1:1,5:3 or similar ratios will secure pharmacological and nutraceutical activity for an extended period of time up to 48 hours.

The composition of these antioxidants according to the present invention is highly suitable for treatments like cardiovascular disease or the prevention of neoplastic growth.

Besides, the antiviral properties of quercetin are also effective in these compositions.

In a preferred embodiment of the present invention the composition comprises isoquercetin and rutin in a molar ration of about 1:4. When administered to humans, this composition will secure up to 24 hours a continued high concentration of flavonols in plasma assuring similar pharmacological activity during the 24-hour time period.

It has been found that these combinations are most effective in prevention of and in defence against stress dysfunctions, especially against oxidative damage of living tissues. Furthermore, the combinations according to this invention will secure pharmacological and nutraceutical effectiveness for an extended period time for specially designed treatments with these specific antioxidants, e.g. treatment of cardiovascular disease, or the prevention of neoplastic growth. The effect of the continuity of their concentrations is obtained by the summation of their specific concentration kinetics in the human body.

The daily dose of the mixture of the flavonols that have the same aglycone is about 100 mg of quercetin glycoside and 400 mg of rutin. It is possible that the dose may be increased to an expected maximum of about 400 mg of quercetin glycoside and 1600 mg of rutin, maintaining the proportion of flavonols of 1:4 as discussed above. For the mixture of isoquercetin or quercetin-4'-glucoside, quercetin and rutin in the molar ratio of 1:1,5:3 a similar daily dose is suggested like about 100 mg quercetin glycoside, 150 mg of quercetin and 300 mg of rutin up to a maximum dose of about 400 mg of quercetin glycoside, 600 mg of quercetin and 1200 mg of rutin, always maintaining the proportion.

The compositions according to the present invention may be used in form of tablets, capsules or syrups with usable excipients.

The compositions of the present invention preferably are useful as food supplements, but they may also be administered in a pharmaceutical treatment.

The present invention makes available:
- a method of maintaining a continued presence of high concentrations of bioflavonols in human plasma for an extended period of time,
- a method of protection against oxidative damage to human organs, tissues and cells,
- a method of supporting a pharmacological treatment of a disease or dysfunction caused by oxidative damage,
- a method of prevention of cardiovascular diseases, and other damage to vascular tissues, of bacterial and viral infections, of metabolic dysfunctions involving oxidative damages or of neoplastic growth, by oral administration of a composition described above.

The decision which further ingredients should be components of a composition useful in one of the above-mentioned methods depends on the special indication. Usually, if the composition is administered as a way of protection or prevention, useful further ingredients may be vitamins, salts of Mg, Ca, K, Fe and trace elements in known amounts as used in food supplements. Compositions useful in a method of supporting pharmacological treatments may differ from them.

Therefore, a highly efficient dietary antioxidant composition is prepared using among other ingredients the mixtures of isoquercetin or quercetin-4'-glycoside and rutin, optionally together with quercetin. The advantageous properties of these compositions are induced by the effect of building a kind of bioflavanoid complex with delayed release of the bioflavonols.

A subject of this invention is that in humans the oral administration of a mixture of isoquercetin or quercetin-4'-glycoside and rutin, optionally together with quercetin, with a suitable molar ratio described above, conveys sufficient protection against oxidative damages, due to a continued presence of bioflavonols assuring similar pharmacological and nutraceutical activity during a prolonged period of time.

The entire disclosure of all applications, patents and publications, cited above and below are hereby incorporated by reference.

BRIEF DESCRIPTION OF THE DRAWINGS

The FIGURE shows the concentration of rutin, isoquercetin and their total concentration as a function of time.

From the foregoing description, one skilled in the art can easily ascertain the essential characteristics of this invention and, without departing from the spirit and scope thereof, can make various changes and modifications of the invention to adapt it to various applications and conditions.

EXAMPLE 1

A composition according to this invention is prepared by mixing 400 mg rutin with 100 mg isoquercetin. The results of this formula are shown in diagram 1.

What is claimed is:

1. A composition suitable for oral administration comprising isoquercetin and rutin, wherein the isoquercetin to rutin molar ratio is about 1:4.

2. A composition according to claim 1 containing a sufficient amount of isoquercetin and rutin, wherein when administered to a human, said composition maintains a concentration of isoquercetin and rutin in plasma for about 7 to 24 hours sufficient to achieve essentially constant pharmacological and nutraceutical activity of said isoquercetin and rutin.

3. A composition according to claim 1 further comprising quercetin.

4. A composition for oral administration comprising isoquercetin or quercetin-4'-glycoside; quercetin; and rutin.

5. A composition according to claim 4, comprising isoquercetin or quercetin-4'-glycoside, quercetin and rutin in a molar ratio of about 1:1.5:3.

6. A composition according to claim 4 containing a sufficient amount of isoquercetin and rutin, wherein when administered to a human, said composition maintains a concentration of isoquercetin and rutin in plasma for about 7 to 48 hours sufficient to achieve essentially constant pharmacological and nutraceutical activity of said isoquercetin and rutin.

7. A method of maintaining a concentration of isoquercetin and rutin in plasma for about 7 to 24 hours sufficient to achieve essentially constant pharmacological and nutraceutical activity of said isoquercetin and rutin comprising orally administering a composition according to claim 1.

8. A method of protecting against oxidative damage to human organs, tissues and cells comprising orally administering a composition according to claim 1 to a patient in need thereof.

9. A method of treating a disease or dysfunction caused by oxidative damage, comprising orally administering a composition according to claim 1.

10. A method of orally administering a composition according to claim 1 in the form of a food supplement.

11. A pharmaceutical composition comprising the composition of claim 1, a pharmaceutically active ingredient other than isoquercin and rutin, a pharmaceutically active ingredient, and a pharmaceutically acceptable carrier.

12. A method of maintaining a concentration of isoquercetin and rutin in plasma for about 7 to 24 hours sufficient to achieve the essentially constant pharmacological and nutraceutical activity of said isoquercetin and rutin comprising orally administering a composition according to claim 4.

13. A method of protecting against oxidative damage to human organs, tissues and cells comprising orally administering a composition according to claim 4 to a patient in need thereof.

14. A method of treating a disease or dysfunction caused by oxidative damage, comprising orally administering a composition according to claim 4 to a patient in need thereof.

15. A method of orally administering a composition according to claim 4 in the form of a food supplement.

16. A pharmaceutical composition comprising the composition of claim 1, a pharmaceutically active ingredient other than isoquercetin and rutin, a pharmaceutically active ingredient, and a pharmaceutically acceptable carrier.

17. A composition according to claim 1, wherein when administered to a human, a daily dose of about 100 to 400 mg of isoquercetin and about 400 to 1600 mg of rutin is administered to said human.

18. A composition according to claim 1, wherein when administered to a human, a daily dose of about 100 mg of isoquercetin and about 400 mg of rutin is administered to said human.

19. A composition according to claim 4, wherein when administered to a human, a daily dose of about 100 to 400 mg of isoquercetin, about 150 to 600 mg of quercetin and about 300 to 1200 mg of rutin is administered to said human.

20. A composition according to claim 4, wherein when administered to a human, a daily dose of about 100 mg of isoquercetin, about 150 mg of quercetin and about 300 mg of rutin is administered to said human.

21. A method of treating a cardiovascular disease, comprising orally administering a composition according to claim 1 to a patient in need thereof.

22. A method of treating a cardiovascular disease comprising orally administering a composition according to claim 4 to a patient in need thereof.

* * * * *